United States Patent
Vedage et al.

[11] Patent Number: 6,140,540
[45] Date of Patent: *Oct. 31, 2000

[54] HYDROGENATION OF AROMATIC AMINES TO PRODUCE THEIR RING HYDROGENATED COUNTERPARTS

[75] Inventors: Gamini Ananda Vedage, Bethlehem; Richard Scott Myers, Kutztown; John Nelson Armor, Orefield, all of Pa.

[73] Assignee: Air Products and Chemicals, Inc., Allentown, Pa.

[*] Notice: This patent is subject to a terminal disclaimer.

[21] Appl. No.: 08/043,646

[22] Filed: Apr. 6, 1993

[51] Int. Cl.⁷ .................................................. C07C 209/00
[52] U.S. Cl. ........................... 564/451; 564/444; 564/450
[58] Field of Search .................... 564/444, 450, 564/451

[56] References Cited

U.S. PATENT DOCUMENTS

| | | | |
|---|---|---|---|
| 2,511,028 | 6/1950 | Whitman | 564/451 |
| 2,606,924 | 8/1952 | Whitman | 564/451 |
| 2,606,925 | 8/1952 | Whitman | 564/450 |
| 2,606,928 | 8/1952 | Barkdoll et al. | 564/451 |
| 3,117,992 | 1/1964 | Duggan | 564/450 |
| 3,155,724 | 11/1964 | Arthur | 564/444 |
| 3,347,917 | 10/1967 | Arthur | 564/451 |
| 3,445,516 | 5/1969 | Cross | 564/451 |
| 3,520,928 | 7/1970 | Greco | 564/450 |
| 3,558,703 | 1/1971 | Adam et al. | 564/451 |
| 3,591,635 | 7/1971 | Farrissey et al. | 564/451 |
| 3,634,512 | 1/1972 | Peebler et al. | 564/451 |
| 3,679,746 | 7/1972 | Brake | 564/444 |
| 3,711,550 | 1/1973 | Brake | 564/444 |
| 3,743,677 | 7/1973 | Grosskiasky et al. | 564/451 |
| 3,766,272 | 10/1973 | Brake | 564/444 |
| 3,799,983 | 3/1974 | Corr et al. | 564/451 |
| 3,829,490 | 8/1974 | Mueller et al. | 564/444 |
| 4,020,104 | 4/1977 | Richter | 564/444 |
| 4,439,544 | 3/1984 | Carter et al. | 502/234 |
| 4,503,249 | 3/1985 | Nowack et al. | 564/385 |
| 4,946,998 | 8/1990 | Casey | 564/451 |
| 5,214,212 | 5/1993 | Whitman | 564/451 |

FOREIGN PATENT DOCUMENTS

| | | | |
|---|---|---|---|
| 053818 | 6/1982 | European Pat. Off. | 564/450 |
| 1122609 | 8/1968 | United Kingdom . | |

*Primary Examiner*—Samuel Barts
*Attorney, Agent, or Firm*—Mary E. Bongiorno

[57] ABSTRACT

This invention relates to an improved hydrogenation and isomerization process wherein aromatic amines are hydrogenated to their ring hydrogenated counterparts and substantially isomerized to their thermodynamic form. These aromatic amines are presented by the formulas:

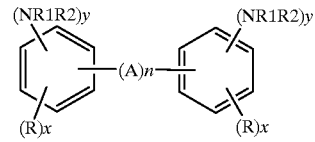

I

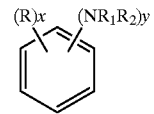

II wherein R is hydrogen or $C_{1-6}$ alkyl, R1 and R2 are hydrogen or $C_{1-6}$ aliphatic, A is $C_{1-4}$ or NH; n is 0–2, x is 1–3 and y is 0 to 2 except the sum of the y groups must be at least 1.

10 Claims, No Drawings

HYDROGENATION OF AROMATIC AMINES TO PRODUCE THEIR RING HYDROGENATED COUNTERPARTS

TECHNICAL FIELD

This invention pertains to a process for hydrogenating aromatic amines to produce their ring hydrogenated counterparts.

BACKGROUND OF THE INVENTION

There is substantial literature in the art with respect to the hydrogenation of aromatic amines, including bridged aromatic amines, e.g., methylenedianiline to produce 4,4'-methylenedi(cyclohexylamine), also referred to as bis(para-aminocyclohexyl)methane (PACM), and bis(4-aminocyclohexyl)methane. The hydrogenated form of these aromatic amines, typically exist as a mixture of isomers, e.g., the cis,cis- (c,c); cis,trans- (c,t) and trans,trans- (t,t). Often it is desirable to produce a product having a specific isomer content, as the isomer content in the mixture not only influences the physical form of the product but also influences the properties of products in which they are incorporated. In the case of PACM, a low trans,trans- isomer content (20%) in the mixture, commonly referred to as PACM-20, exists as a liquid product while a mixture high in trans,trans-isomer content (50%), commonly referred to as PACM-48, leads to a solid form. For certain applications, such as the manufacture of polyamide fibers and epoxy additives, it often is beneficial to use PACM-48 instead of PACM-20.

Commercially, PACM-48 is produced through continuous processing conditions, where catalyst loading and reactor residence times are sufficient to yield the product of thermodynamic control. Batch processing conditions produce PACM-48 from MDA inefficiently due to excessive reaction times required for complete isomerization to the product of thermodynamic control.

Some of the early hydrogenation work to produce cycloaliphatic amines, such as, PACM, was done by Whitman and Barkdoll, et al. and their work is set forth in a series of e.g., U.S. Pat. Nos. 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80 to 275° C. utilizing a ruthenium catalyst. The hydrogenation is carried out under liquid phase conditions and an inert organic solvent is used in the hydrogenation process. Typically, a liquid product having a trans,trans- isomer content of 15–23% is obtained. Examples of ruthenium catalysts utilized for the hydrogenation process include ruthenium oxides such as ruthenium sesquioxide and ruthenium dioxide; and ruthenium salts.

Brake, et al. in U.S. Pat. Nos. 3,696,108 and 3,644,522 continued in the development of processes for manufacturing PACM by hydrogenating methylenedianiline. They found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation.

U.S. Pat. Nos. 3,347,917; 3,711,550; 3,679,746; 3,155,724; 3,766,272 and British Patent 1,122,609 disclose various hydrogenation and isomerization processes to produce PACM containing high trans,trans- isomer content; i.e. an isomer content near equilibrium, typically 50% trans,trans-, 43% cis,trans- and 7% cis,cis-. As in the early work ruthenium catalysts usually were used to effect isomerization. High temperatures and long reaction times were required to produce the high trans,trans- isomer product and, in addition, considerable deamination of product took place.

A wide variety of catalytic systems have been developed for the hydrogenation of aromatic amines, and typical catalytic systems are represented in the following patents:

U.S. Pat. No. 3,591,635 discloses the use of rhodium on alumina as a catalyst for the hydrogenation of methylenedianiline.

U.S. Pat. No. 4,946,998 discloses processes for the hydrogenation of methylenedianiline contaminated with impurities utilizing a mixture of rhodium and ruthenium as the catalyst. A hydrogenated methylenedianiline product having a trans,trans- isomer content of from about 14 to 28% is prepared using the mixed metal catalyst system, although higher trans,trans- content can be achieved through high temperature, long reaction times, and high ruthenium concentration. The presence of rhodium permits lower operating temperatures and reduces the percent trans,trans- isomer in the reaction product.

U.S. Pat. No. 3,520,928 discloses the low pressure hydrogenation of mineral acid salts of aromatic primary amines and aqueous solution using a platinum or palladium catalyst.

U.S. Pat. No. 3,558,703 and U.S. Pat. No. 3,634,512 disclose the high pressure catalytic hydrogenation of diaminodiphenylalkanes and ethers utilizing a cobalt or nickel catalyst promoted with manganese and base modified derivatives thereof ('512). The '703 patent discloses that other conventional catalysts may be incorporated into the catalyst component of cobalt or nickel, and such metals include copper, chromium, nickel, tungsten, molybdenum, platinum, palladium and ruthenium in amounts up to about 10% by weight.

U.S. Pat. No. 3,445,516 discloses the hydrogenation of toluenediamine utilizing a variety of catalysts including Raney nickel, Raney cobalt, cobalt oxide and mixtures of cobalt oxide and alkaline earth metal oxide, such as calcium oxide in combination with sodium carbonate.

SUMMARY OF THE INVENTION

This invention relates to an improved process for producing cycloaliphatic amines such as 4,4'-methylenedi(cyclohexylamine) (PACM) by the catalytic hydrogenation of such aromatic amines to produce their hydrogenated and thermodynamically stable isomeric counterparts. The improvement in the hydrogenation process comprises using a catalytic system comprising cobalt in combination with another Group VIII metal, the metal generally being selected from rhodium, ruthenium, platinum, and palladium. Preferably the catalyst comprises cobalt in combination with rhodium or ruthenium. As a catalyst the weight ratio of Group VIII metal, particularly rhodium or ruthenium, to cobalt is from 0.2 to 5, preferably 1 to 2.

There are several advantages associated with this process. These include:

an ability to hydrogenate aromatic amines to ring hydrogenated counterparts in high selectivity;

an ability to effect hydrogenation and isomerization of aromatic amines at relatively low pressures e.g. 1500 psig and lower at acceptable reaction rates;

an ability to hydrogenate and isomerize bridged dianilines to a product having an isomer distribution approximating that of the thermodynamic form;

an ability to hydrogenate and isomerize bridged aromatic amines without effecting significant deamination of the feed or product; and, an ability to use the catalyst for continued periods of time with only modest maintenance or regeneration techniques.

DETAILED DESCRIPTION OF THE INVENTION

This invention relates to an improvement in the conventional ring hydrogenation and isomerization of aromatic amines and these amines are represented by the formulas:

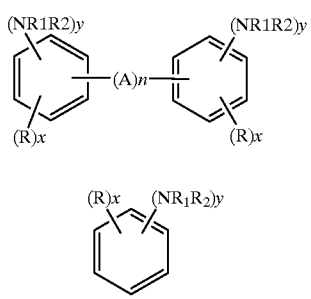

wherein R is hydrogen or $C_{1-6}$ alkyl, R1 and R2 are hydrogen, or $C_{1-6}$ alkyl, A is $C_{1-4}$ alkyl, or NH, n is 0 or 1, x is 1–3 and y is 0–2 except the sum of the y groups in the formulas must be at least 1. By the practice of this invention, one is able to selectively produce a ring hydrogenated reaction product in high selectivity with excellent reaction rates.

The aromatic amines useful in the practice of the process are bridged polynuclear aromatic amines or mononuclear aromatic amines. These can be substituted with various substituents such as alkyl groups containing from 1–6 carbon atoms. Further, the amine group can be substituted with alkyl groups or alkanol groups resulting in secondary and tertiary amines. Examples of bridged aromatic amines include methylene dianilines such as bis(para-aminophenyl) methane (MDA) including up to about 15% anilineformaldehyde oligomers by weight; bis(4-amino-3-methylphenyl) methane; bis(diaminophenyl)methane; bis(diaminophenyl) propane; biphenylamine; tolidine; N—$C_{1-4}$-aliphatic derivatives and N,N'$C_{1-4}$ aliphatic secondary and tertiary amine derivatives of the above bridged aromatic amines. Examples of mononuclear aromatic amines include 2,4- and 2,6-toluenediamine, alkylated derivatives of toluenediamine, such as, 1-methyl-3,5-diethyl-2,4 or 2,6-diaminobenzene, commonly known as diethyltoluenediamine; diisopropyltoluenediamine, mono-isopropyl toluenediamine, tert-butyl-2,4-and 2,6-toluenediamine, cyclopentyl-toluenediamine; phenylenediamine, and alkylated derivatives of phenylenediamine and aniline, e.g., ortho-toluidine, ethyl toluidine, xylenediamine, mesitylene diamine, and the N and N,N'$C_{1-4}$ aliphatic secondary and tertiary amine derivatives of the mononuclear aromatic monoamines and mononuclear aromatic diamines. The hydrogenation and isomerization process is carried out under liquid phase conditions, such liquid phase conditions being maintained typically by carrying out the hydrogenation in the presence of a solvent. Although as reported in the art, it is possible to produce the reaction product in the absence of a solvent, the processing usually is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetra-hydrofuran, dioxane, dicyclohexyl ether and glyme polyethers. Tetra-hydrofuran is preferred. Although in some processes water can be used as a cosolvent, it is preferred that the system be maintained in an anhydrous state or at least maintained such that the water concentration is less than 0.5% by weight. Water, when present in the system, tends to increase the amount of by-product alcohols and heavy condensation products and it tends to deactivate the catalyst system.

When a solvent is used, concentrations as low as 50% by weight based upon the aromatic amine introduced into the reaction zone are common and typically the solvent is used at levels from about 75 to about 500% by weight of the starting compound. High solvent use has associated recovery burdens.

The hydrogenation is carried out principally in a batch process although it is possible to operate the plant continuously. Temperatures for the hydrogenation and isomerization process range from about 130 to 220° C. with preferred temperatures of from about 170 to 195° C. In contrast to the prior art hydrogenation and isomerization processes, particularly for the hydrogenation and isomerization of bridged anilines using cobalt as a catalyst, where hydrogen partial pressures typically range from about 2500 to 4000 psig, this process employs pressures as low as from about 500 to 1500 psig, even with systems containing impurities such as oligomers of MDA. The ability to operate at lower pressures reduces equipment costs and lowers operating costs.

The ability to ring hydrogenate aromatic amines and particularly methylenedianiline at low hydrogen partial pressures while producing an isomer distribution approaching thermodynamic equilibrium, with excellent reaction rates is achieved by the utilization of a specific hydrogenation/isomerization catalyst system. The catalyst utilized in the hydrogenation/isomerization process comprises cobalt in combination with a Group VIII metal. To effect hydrogenation, the weight ratio of Group VIII metal to cobalt broadly is from 0.2 to 5, preferably 1 to 2 with the Group VIII metal preferably being ruthenium or rhodium.

In a preferred embodiment the cobalt component of the catalyst system is present as a bimetallic mixture comprising cobalt and a Group VIII metal or copper. When cobalt is present as the bimetallic mixture, the reduction temperature of the cobalt catalyst portion of the catalyst system is lowered and reduction with hydrogen may be effected at temperatures as low as 200° C. When the cobalt is not present as a bimetallic mixture, and carried on a separate support, e.g., alumina, silica, titania, or other conventional materials, the cobalt reduction temperature remains high, e.g., 400° C. and above. The bimetallic cobalt catalyst component can be prepared by coprecipitating a portion of the Group VIII metal, as a salt, with the cobalt salt. In addition to the above metals which can be used in forming the bimetallic cobalt component of the catalyst, copper, may be used as a component for producing the cobalt component of the catalyst system. A level of 0.2 to 100, preferably 3 to 60 weight parts cobalt per weight part copper, may be used.

This catalyst system, in contrast to cobalt alone or in contrast to other Group VIII metals alone, permits hydrogenation of the aromatic amines at low pressures, and permits isomerization of hydrogenated bridged aromatic amines, in large part, to the thermodynamic isomer form.

Not only that, many other combinations of Group VIII metals do not give the same isomer distribution or yield. For example, in the case of bis(para-aminophenyl)methane hydrogenation to bis(para-aminocyclohexyl)methane the catalyst mixture of rhodium and ruthenium results in a trans,trans- isomer content, typically between that of rhodium and ruthenium.

The cobalt containing catalyst typically is carried on a support at about 0.25 to 25 weight parts metal, per 100 weight parts of support, e.g., alumina, or titania, preferably 1 to 20 weight parts metal per 100 weight parts support. A catalyst level from 0.1 to 10% by weight of the aromatic amine is utilized with preferred levels being from 0.5 to 5% by weight. When the amount of catalyst approaches the lower limit of the range, the reaction rate may decrease. However, as the concentration of catalyst vis-a-vis the aromatic amine increases the reaction rate will increase up to a point and then level off to a constant rate.

The progress of a hydrogenation reaction can readily be followed by observing the amount of hydrogen taken up by the reaction mixture and the reaction is terminated when the amount of hydrogen absorbed is equal or nearly equal to that amount necessary to effect complete hydrogenation of the substrate. In general, the hydrogenation time for aromatic amines will range from about 100 to 500 minutes, at modest catalyst levels, e.g., 0.5–5% broadly 0.1–10% by weight of the aromatic amine at 180° C. and 850 psig, and generally will not exceed 500 minutes.

Although not intending to be bound by theory, it is believed the unexpected activity and life of the catalyst system, particularly when cobalt is present as a bimetallic mixture, is due to the lowering of the hydrogen reduction temperature of the cobalt. The generation of a reaction product having a high concentration of isomers in the thermodynamically most stable form by using the catalyst system described herein is not readily explained since the isomer distribution is not representative of the average of the isomer distribution with either the Group VIII or cobalt catalyst component alone. For example, reduction of methylenedianiline in the presence of cobalt, is difficult, and if possible, results in a product having a trans,trans- isomer concentration of 40%; in the presence of rhodium alone, the trans,trans- isomer concentration may be 15–25%; and in the presence of ruthenium alone the trans,trans- isomer concentration ranges between 20–40% unless high temperatures, high pressures, and long reaction times are used. Cobalt in combination with either of these metals results in trans, trans- isomer distributions greater than 45% trans,trans- at reduced reaction times and conditions.

The following examples are intended to illustrate various embodiments of the invention and all parts and percentages given are weight parts or weight percents unless otherwise specified.

EXAMPLE 1

Cobalt Catalyst Preparation a. Preparation of 4% $Co/Al_2O_3$ Catalyst

A cobalt catalyst was prepared by adding 1.98 g $Co(NO_3)_2/6H_2O$) to 7 g of deionized (DI) water. To this solution was added 10 g of activated gamma alumina. The catalyst was dried overnight at 100° C. and calcined at 400° C. for 3 hrs in air to obtain the final catalyst.

b. Preparation of 1% Ru/3% $Co/Al_2O_3$ Bimetallic Catalyst

A ruthenium-cobalt bimetallic catalyst was prepared by dissolving a 0.21 g of $Ru_3(CO)_{12}$ in hot THF and then adding 10 g of activated gamma alumina. Excess THF was evaporated with stirring. To this ruthenium solution was added 1.48 g of $Co(NO_3)_2/6H_2O$ dissolved in 7 g of DI water. The mixture was stirred and then placed in a 100° C. oven overnight. The final catalyst, consisting of a cobalt/ruthenium bimetallic, was obtained by calcining the catalyst at 400° C. for 3 hrs.

EXAMPLE 2

Cobalt on Alumina and Ruthenium on Alumina Admixture

A catalyst system was prepared by physically admixing a commercial catalyst system of 5% $Ru/Al_2O_3$ and 4% $Co/Al_2O_3$ in a weight proportion of 5 parts of ruthenium metal to 4 weight parts of the cobalt metal.

Other catalyst systems can be prepared in essentially the same way as described in these Examples 1 and 2. Alternatively, procedures used in the prior art may be used to prepare the catalyst systems.

EXAMPLE 3

Catalyst Prereduction Technique

1. Catalyst Pretreatment a. Prereduction at 200° C.

Prior to catalyst use, each catalyst undergoing 200° C. reduction was charged to an empty, clean 300 cc autoclave reactor. Isopropanol (125 g) was added to the reactor and the autoclave sealed, leak tested, purged three times with nitrogen (pressurized to >200 psig, agitated, and then vented to atmospheric pressure with the agitator off). The reactor then was purged three times with hydrogen to 850 psig and vented. After venting, the reactor was pressurized to 750 psig and heated to 192° C. The system was held at temperature for two hours, cooled, vented and purged three times with nitrogen. The catalyst was recovered by filtering the mixture under a nitrogen atmosphere.

b. Prereduction at 500° C.

In a procedure similar to catalyst prereduction at 200° C., each catalyst was charged to a ½" ID tubular reactor. (The autoclave was not suited for 500° C. temperatures.) Hydrogen was passed through the reactor at a rate of 20–30 cc/min. After 10 min of purging, the reactor was heated to 500° C. The system was held at temperature for 1 hr, cooled to room temperature, and purged with nitrogen for 30 min. The catalyst was then recovered in air at room temperature.

EXAMPLE 4

Catalyst Comparison in MDA Hydrogenation Reaction Procedure

A 300 cc autoclave batch reactor was used to carry out the hydrogenation of MDA. All runs were at 180° C. and 850 psig pressure at 1500 rpm stirring rates to minimize hydrogen mass transfer as a limitation to reaction rates.

A desired amount of pre-reduced catalyst charge was added to the pressure vessel followed by the addition of MDA in THF. The autoclave was sealed, purged with excess nitrogen, followed with hydrogen and pressurized to about 600 psig with hydrogen. The autoclave was heated with agitation to the specified reaction temperature with addition of hydrogen from a ballast tank to maintain a pressure of 850 psig. The drop in pressure in the ballast tank provided a convenient method for observing the progress of the reaction with the reaction being considered complete when hydrogen consumption stopped. After the reaction was complete, the autoclave was cooled to room temperature, vented and the product mixture removed. The product was analyzed by capillary GC previously calibrated for the materials involved. Table 1 notes catalyst type, reaction conditions and yield and also provides results for the catalytic hydrogenation of crude methylenedianiline or MDA-85 (15% oligomer) at 180° C. and 850 psig.

physical admixture of cobalt and Group VIII metal, the cobalt requiring a higher activation temperature.

Run 8 shows that 4% Rh/Al$_2$O$_3$ is an effective hydrogenation catalyst but is a poor isomerization catalyst. Run 7 shows that the physical mixture of 4% Rh/Al$_2$O$_3$ and the Co/Rh bimetallic catalyst is effective for hydrogenation of MDA to PACM-48.

TABLE 1

HYDROGENATION OF METHYLENEDIANILINE

| Run | Catalyst* | Pre Treat ° C. | Ratio M:Co[f] | % Cat[b] | Time Min | % Conv | % PACM | % Half PACM[c] | % t/t |
|---|---|---|---|---|---|---|---|---|---|
| 1 | 5% Ru | 200 | — | 1.5 | 430 | 98.4 | 90.5 | 3.3 | 38.8 |
| 2 | 4% Co | 500 | — | 1.5 | 430 | 10.2 | 0.8 | 17.5 | — |
| 3 | 5% Ru + 4% Co | Ru = 200 Co = 500 | 5:4 | 3.0 | 410 | 100 | 92.2 | 0 | 53.1 |
| 4 | 5% Ru + 4% Co[e] | 200 | 5:4 | 1.5 | 430 | 38.8 | 8.6 | 54.5 | 14.9 |
| 5 | 3% Co/1% Ru + 5% Ru | 200 | 2:1 | 3.0 | 390 | 100.0 | 93.1 | 0.0 | 53.8 |
| 6 | 3% Co/1% Rh | 200 | 1:3 | 1.5 | 430 | 63.7 | 27.2 | 59.4 | 49.3 |
| 7 | 4% Rh + 3% Co/0.25% Rh | 200 | 4.25:3 | 3.0 | 200 | 99 | 93.7 | 1.2 | 45.0 |
| 8 | 4% Rh | 200 | — | 1.5 | 210 | 99 | 94.1 | 1.2 | 19.4 |

HYDROGENATION OF CRUDE METHYLENEDIANILINE[d] CONDITIONS 180° C. AT 850 PSIG

| Run | Catalyst* | Pre Treat ° C. | Ratio M:Co | Use | % Cat | Time Min | % Conv | % PACM | % Half PACM | % t/t |
|---|---|---|---|---|---|---|---|---|---|---|
| 9 | 5% Ru | 200 | — | 1 | 1.5 | 430 | 65.7 | 24.5 | 54.8 | 21.4 |
| 10 | 5% Ru | 200 | — | 1 | 2.5 | 500 | 85.0 | 56.5 | 29.3 | 33.7 |
| 11 | 5% Ru + 3% Co/1% Ru | 200 | 2:1 | 1 | 2.5/ 1.5 | 495 | 96.7 | 84.8 | 6.9 | 52.5 |
| 12 | 5% Ru + 3% Co/1% Ru | " | " | 2 | 2.5/ 1.5 | 480 | 98.2 | 86.9 | 3.6 | 54.0 |

[a]All catalysts were carried on a gamma alumina support unless otherwise noted.
[b]Catalyst weight given as a percentage of methylenedianiline.
[c]Refers to the product derived from MDA by the uptake of 3 mole equivalent of hydrogen, or 4(4-aminobenzyl)cyclohexylamine.
[d]crude methylenedianiline has 85% methylenedianiline and 15% oligomers.
[e]physical mixture.
[f]metal to cobalt weight ratio.

Comments regarding Table 1

Run 2 shows that a single catalyst system of cobalt, 4% Co/Al$_2$O$_3$, was ineffective. When MDA was hydrogenated at low pressure using 4% Co/Al$_2$O$_3$ (500° C. reduced), only 10% of the hydrogenation was completed in 430 minutes with only traces of PACM being produced. The major product formed during the hydrogenation of MDA using 4% Co/Al$_2$O$_3$ catalyst is the half hydrogenated MDA.

Run 3 shows that the physical mixture of 5% Ru/Al$_2$O$_3$ and 4% Co/Al$_2$O$_3$ reduced at 500° C. (Ru:Co=5:4), completed the MDA hydrogenation in 410 min with greater than 90% PACM yield and with a 53% trans/trans-isomer content. A second use of the catalyst for MDA hydrogenation gave 90% PACM yield with 52% trans/trans-isomer content (not shown in the Table). This result indicates that the catalyst does not deactivate in the first two uses. Run 5 shows that the physical mixture of 5% Ru/Al$_2$O$_3$ and the bimetallic catalyst (Co/Ru) is effective for converting MDA to PACM-48 prereduced at 200° C. The addition of the second metal (Rh, Ru, Pd, or Cu) to cobalt, as in the bimetallic form of catalyst, renders cobalt easily reducible at 200° C. This allows the physical mixture of Ru and the bimetallic catalyst (Co/Ru) to produce PACM-48 from MDA with catalysts prereduced at 200° C. That same characteristic is not found in the catalyst comprising the Runs 9 & 10 show that ruthenium, as a catalyst, is relatively in-effective for hydrogenation and isomerization of crude MDA to PACM-48 at low pressures. These results are consistent with prior art processes.

Runs 11 and 12 show that a physical mixture of 5% Ru/Al$_2$O$_3$ and 3% Co/1% Ru/Al$_2$O$_3$ (Ru:Co=2:1) is very active for hydrogenation/isomerization of crude MDA to PACM-48.

The above results also show that a physical admixture of Co/Al$_2$O$_3$ and Ru/Al$_2$O$_3$ or Rh/Al$_2$O$_3$ is an effective catalyst for the production of an equilibrium mixture of PACM isomers if the Co/Al$_2$O$_3$ catalyst is reduced at 400° C., or higher, in the presence of hydrogen. This can be contrasted with the result obtained from Run 4 where Co/Al$_2$O$_3$ was treated at 200° C. and only partial conversion (38.8%) with low t/t isomers (14.9) was obtained.

What is claimed is:

1. In a process for the catalytic hydrogenation/ isomerization of aromatic amines represented by Formula I,

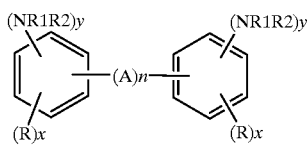

wherein R, R1 and R2 are hydrogen or $C_{1-6}$ aliphatic, A is $C_{1-4}$ alkyl, n is 0–1, x is 1–3, and y is 1–2, to their ring hydrogenated counterparts, by contacting the aromatic amines with hydrogen in the presence of a catalyst, the improvement which comprises effecting said hydrogenation/isomerization with a catalyst comprising a physical mixture of cobalt and a metal selected from the group consisting of rhodium, ruthenium, palladium, and platinum.

2. The process of claim 1 wherein the catalyst is present in an amount from about 0.1 to 10% by weight of the aromatic amine.

3. The process of claim 2 wherein the weight ratio of cobalt to metal ranges from about 0.2 to 5 parts by weight metal, per weight part cobalt.

4. The process of claim 3 wherein R1 and R2 are hydrogen.

5. The process of claim 4 wherein A is —$CH_2$— and n is 1.

6. The process of claim 5 wherein hydrogenation is conducted at a hydrogen pressure from about 500 to 1500 psig.

7. The process of claim 6 wherein the catalyst comprises a bimetallic mixture of cobalt and rhodium and the ratio of cobalt to rhodium as metal, is from about 1–2 weight parts rhodium per weight part cobalt.

8. The process of claim 6 wherein the catalyst comprises ruthenium or rhodium as the metal and the cobalt component is present as a bimetallic mixture of cobalt and copper and the ratio of cobalt to copper as metal, is from about 0.2 to 100 weight parts cobalt per weight part copper.

9. In a process for the catalytic hydrogenation/isomerization of crude methylenedianiline containing up to about 15% of oligomer by weight to bis-(4-aminocyclohexyl)methane, which comprises hydrogenating/isomerizing the methylenedianiline in the presence of a catalyst system, the improvement which comprises effecting said hydrogenation/isomerization in the presence of a catalyst comprising cobalt and a metal selected from the group consisting of rhodium and ruthenium and at least a portion of the cobalt catalyst component is present as a bimetallic mixture.

10. The process of claim 9 wherein the catalyst system comprising cobalt and rhodium or ruthenium or both and the amount of rhodium or ruthenium or both is from 1 to 20 weight parts per weight part cobalt, and the amount of catalyst based on methylenedianiline is from 0.5 to 5% by weight.

* * * * *